United States Patent
Choudary et al.

(10) Patent No.: US 6,472,555 B2
(45) Date of Patent: *Oct. 29, 2002

(54) PROCESS FOR THE PRODUCTION OF ESTERS FROM ALCOHOLS USING ACETIC ACID AS ACETYLATING AND CLAYS AS CATALYSTS

(75) Inventors: Boyapati Manoranjan Choudary; Veldurthy Bhaskar; Mannepalli Lakshmi Kantam; Kottapalli Koteswara Rao; Kondapuram Vijaya Raghavan, all of Andhra Pradesh (IN)

(73) Assignee: Council of Scientific and Industrial Research, Rafi Marg (IN)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/250,385

(22) Filed: Feb. 12, 1999

(65) Prior Publication Data

US 2001/0016666 A1 Aug. 23, 2001

(30) Foreign Application Priority Data

Dec. 24, 1998 (IN) ........................................ 3826/DEL/98

(51) Int. Cl.$^7$ .............................................. C07C 69/02
(52) U.S. Cl. ........................ 560/231; 560/250; 560/252; 560/253; 560/254; 560/261; 560/262; 560/265; 560/63; 560/103; 560/204

(58) Field of Search .......................... 560/63, 103, 204, 560/231, 254, 250, 252, 261, 262, 265

(56) References Cited

U.S. PATENT DOCUMENTS

| | | | | |
|---|---|---|---|---|
| 2,928,853 A | * | 3/1960 | Bond | 554/170 |
| 3,014,066 A | * | 12/1961 | Kerr et al. | 560/247 |
| 3,096,365 A | * | 7/1963 | Heisler et al. | 560/247 |
| 3,278,585 A | * | 10/1966 | Baker et al. | 560/63 |
| 3,590,073 A | * | 6/1971 | Carr et al. | 560/103 |
| 4,304,925 A | * | 12/1981 | Watanabe et al. | 560/247 |
| 4,440,958 A | * | 4/1984 | Gregory et al. | 560/247 |

* cited by examiner

Primary Examiner—Gary Geist
Assistant Examiner—Taylor V Oh
(74) Attorney, Agent, or Firm—Baker Botts LLP

(57) ABSTRACT

The present invention relates to a process for the preparation of esters from alcohols using acetic acid as acetylating agent and clays as catalysts, which comprises the preparation of esters in a single step from the reaction of aliphatic, acyclic, cyclic, heterocyclic, α,β-unsaturated and aromatic alcohols with carbon atoms in the range of $C_1$ to $C_{10}$ with acetic acid in a molar ratio of 1:3 to 11 using reusable natural montmorillonite/metal ion-exchanged clay catalysts in the solvent medium of aliphatic, aromatic, or chlorinated hydrocarbons at 30–140° C. for a period in the range of 0.02 to 3.0 hrs, and recovering the corresponding esters by simple work-up procedure.

7 Claims, No Drawings

PROCESS FOR THE PRODUCTION OF ESTERS FROM ALCOHOLS USING ACETIC ACID AS ACETYLATING AND CLAYS AS CATALYSTS

FIELD OF THE INVENTION

The present invention relates to a process for the production of esters from alcohols using acetic acid as the acetylating agent and clays as catalysts.

This invention particularly relates to an ecofriendly process for the production of esters from aromatic, aliphatic, α,β-unsaturated, cyclic and heterocyclic alcohols in the range of $C_1$ to $C_{10}$ using acetic acid as the acetylating reagent and clays as catalysts dispensing the use of expensive acetic anhydride as a reagent and corrosive and toxic sulfuric acid, sulfonic acids or expensive resins as catalysts. This process totally eliminates the disposal of salts formed consequent to the neutralisation of $H_2SO_4$ or sulfonic acids and the use of expensive acetic anhydride.

BACKGROUND

Organic esters belong to a very important class of chemicals having applications as intermediates in the synthesis of fine chemicals, drugs, plasticizers, perfumes, food preservatives, cosmetics, pharmaceuticals, as solvents and chiral auxiliaries. In industry, the esterifications are generally carried out in the presence of hazardous, toxic and corrosive sulfuric acid and its derivatives or expensive ion exchange resins. To optimise the yields of ester formation from equimolar amounts of alcohols and carboxylic acids, 2–15 molar equivalents of the condensing agents such as sulfuric acid, tosylchloride, triofluoroacetic anhydride, polyphosphate ester, dicyclohexyl cabodiimide, graphite etc., are generally employed. Heterogeneous acidic and superacid catalysts have proved to be useful in some reactions because of their activity, selectivity, reusability, non-corrosivity and virtual absence of effluent treatment which is associated with the homogeneous catalysts.

Reference may be made to a patent CS 254, 048 (C1, C07C 69/14), Nov. 15, 1988, wherein the esterification of BuOH with AcOH at reflux temperature of 79 to 80° C. in the presence of $H_2SO_4$ catalyst, resulted in butylacetate with 89–90% yield. Reference may be made to a patent CN 1,068,520 (C1. B 01 J 23/10), Feb. 03, 1993, wherein the isopentyl alcohol esterification with AcOH at $\geq 140°$ C. and 100–142 hrs resulted in isopentyl acetate with $H_2SO_4$ treated pulverised rare earth compounds as catalysts. The drawbacks in the above processes are longer reaction time, higher reaction temperatures and the use of corrosive sulphuric acid which requires the waste disposal consequent to the neutralisation with bases after the completion of the reaction.

The solid acids, solid super acids and cation exchange resins are very effective catalysts for the esterification process. Reference may be made to a patent, U.S. Pat. No. 3,590,073 (C1. 260–476 R, C07 C), Jun. 29, 1971, wherein the esterification of tert-BuOH with AcOH, was carried out by passing through a column of Amberlyst-15 (the sulfuric acid treated cation exchange resin) at the rate of 0.5 ml/min at ambient temperature to give 25% tert-butyl acetate. Reference may be made to an European patent, EP 66,059 (C1. C07 C69/14), Dec. 08, 1982, wherein the alcohols with 2–5 carbon atoms react with acetic acid in verticle reactor to give corresponding esters in presence of strongly acid ion exchangers as catalysts. Reference may be made to a patent Rom. Ro 72,739 (C1. C07 C 69/14) Jul. 27, 1981, wherein the esterification of β-phenyl ethyl alcohol with AcOH to give an ester in presence of cation exchangers. The drawbacks in the above processes are the use of expensive resins as catalysts, applicable to 1–5 carbon atoms consisting substrates, higher reaction temperatures and lower conversions with poor yields.

Reference may be made to another communication in *Synthesis.* 1978 (12) 929–30, wherein the esterification of primary and secondary alcohols with acetic acid was performed in the presence of Nafion-H for 4 hrs, resulting in moderate yields (40–60%). The drawbacks in the above processes are the moderate yields and the use of expensive resin catalyst. Reference may be made to a communication in *J.Org. Chem.* 1996, 61, 4560, wherein the esterification of alcohols with carboxylic acids in the presence of p-nitrobezoic anhydride and acylation of alcohols with acid anhydrides using scandium trifluromethane sulfonate (triflate) catalyst resulting <1 to >95% isolated yields in 0.5 to 5 h. The drawbacks in the above processes are the use of synthetic triflate catalyst and acetic anhydride as an acetylating agent. Reference may be made to another paper in *Chem. Comm* 1996, 2625 wherein various alcohols were acetylated in the presence of acetic anhydride (acetylating agent) and trimethylsilyl-trifluoromethanesulfonate (triflate) as catalyst. The yields obtained were 55 to 100% in 0.007 to 2 h. The drawbacks in the above processes are the use of synthetic triflate catalyst, acetic anhydride as acetylating agent and lower yields. The last reference may be made to a communication in *Ind. Eng. Chem.* Res.1994, 33, 2198, wherein the production of phenethyl acetate and cyclohexyl acetate were performed using a variety of solid acid catalysts such as Amberlyst-15, Filtrol-24, sulfonated zirconia, DTPA/silica and DTPA/carbon and acetic acid as the acylating agent. However, with Amberlyst-15 takes 5 h for 95.5% conversion of phenethyl alcohol while DTPA takes 3 h for a conversion of 100%. The drawbacks in the above process are the use of an expensive resins as catalysts and longer reaction time.

Obviously different approaches have been employed both on laboratory and commercial scale to prepare esters, and the traditional homogeneous catalysed reactions are being less favoured owing to the problems of separation and reuse. The present trend is to develop solid acids from cheaply available sources, and especially of clays.

OBJECTS OF THE INVENTION

The main object of the present invention is to provide a process for the production of esters from alcohols acetic using acid as the acetylating agent and clays as catalysts which obviates the drawbacks as detailed above.

Another object of the present invention is the use of non-corrosive and cheaply available heterogeneous solid acid catalysts for easy adaptability in a continuous process.

Still another object of the present invention is to provide the process which is applicable to various substrates of aliphatic, acyclic, cyclic, heterocyclic α,⊕-unsaturated and aromatic alcohols such as octanol, decanol, 2-octanol, amylalcohol, isoamylalcohol, 2-pentanol, cinnamyl alcohol, benzyl alcohol, trans-2-hexene-1-ol, cyclohexanol, cyclopentanol, 1-phenyl ethanol, p-methoxy-1-phenyl ethanol, p-methyl-1-phenyl ethanol and furfuryl alcohol.

Still another object of the present invention is to provide a process which takes place at lower reaction temperatures.

Yet another object of the present invention is to provide the process in short reaction time intervals.

DETAILED DESCRIPTION OF THE INVENTION

Accordingly, the present invention provides a process for the production of esters from alcohols using acetic acid as the acetylating agent and clays as catalysts which comprises the preparation of esters in a single step from the reaction of aliphatic, acyclic, cyclic, heterocyclic, α,⊕-unsaturated and aromatic alcohols having carbon atoms in the range of $C_1$ to $C_{10}$ with acetic acid in the molar ratios of 1:3 to 11 using reusable natural montmorillonite/metal ion exchanged clay catalysts such as $Fe^{3+}$, $Cu^{2+}$, $Zn^{2+}$, $Al^{3+}$, $Ce^{3+}$ or $Zr^{4+}$-montmorillonites in the solvent medium of aliphatic, aromatic, or chlorinated hydrocarbons or without a solvent for at least at 30–140° C. for a period in the range of 0.02 to 3.0 hrs. and recovering the corresponding esters by simple work-up procedure.

In an embodiment, the catalysts were selected from naturally available clays or metal ion exchange clays such as $Fe^{3+}$, $Cu^{2+}$, $Zn^{2+}$, $Al^{3+}$, $Ce^{3+}$ or $Zr^{4+}$-montmorillonites.

In another embodiment, alcohols with carbon atoms in the range of 1–10 may be used and selected from octanol, decanol, 2-octanol, amylalcohol, isoamylalcohol, 2-pentanol, cinnamyl alcohol, benzyl alcohol, trans-2-hexene-1-ol, cyclohexanol, cyclopentanol, 1-phenyl ethanol, p-methoxy-1-phenyl ethanol, p-methyl-1-phenyl ethanol and furfuryl alcohol.

In still another embodiment, the solvents used for the reactions may be selected from aromatic hydrocarbons such as dichloroethane, acetic acid, chlorobenzene and toluene.

Is still another embodiment, the recovery of the corresponding esters was carried out by separating the catalyst through filtration, the excess acetic acid was neutralised by treating with saturated $NaHCO_3$ solution and removing the aromatic hydrocarbons by concentration in rotavapor.

Preferably, the present process for the preparation of esters from alcohols using acetic acid as acetylating agent and clays/modified clays as catalysts in solvent/without a solvent medium (in the presence or absence of a solvent) at 30° C. for a period of 0.02 to 2.5 h, and recovering the corresponding esters by easy work-up. The clay catalysts used may be selected from metal ion-exchanged montmorillonites/natural montmorillonite clays.

One of the major advantages involved in the present invention is use of abundantly available montmorillonite from nature as a catalyst for the acetylation of various alcohols with acetic acid (acetylating agent), preferably, without any further purification as shown in (example 1b) for the first time. The activity of the natural montmorillonite is comparable with the $Cu^{2+}$-montmorillonite ($Cu^{2+}$-exchanged K10 montmorillonite), which is synthesised from commercial K10 montmorillonite (acid treated montmorillonite—Fluka). K10 montmorillonite as such will lead to too many side products [ethers, olefins(dehydrated product), polymerised products, alkylation on the aromatic solvents used in the reaction] instead of giving the corresponding ester with the alcohol and acetic acid due to its higher acidic strength. Exchange of K10 montmorillonite with metal ions changes the acidic strength of the catalyst which was found to be suitable for the exclusive formation of the desired ester. In industries, the esterifications were generally carried out in presence of the sulfuric acid and resins (ion-exchange) catalysts. The resins are expensive and they loose the activity gradually. In some cases the removal/separation of the catalyst from the product become more problematic due to their rigidity, whereas the cheaply available clay, the natural montmorillonite, overcomes the above problems with consistent activity for several cycles.

Metal ion-exchanged montmorillonite clay catalysts were prepared as described in example 1 and employed them in the esterification of alcohols with Acetic acid (acetylating agent) as described in examples 2 to 21.

The following examples are given by way of illustration of the present invention and therefore should not be construed to limit the scope of the present invention.

EXAMPLE 1

Catalyst Preparation a) $Cu^{2+}$-exchanged montmorillonite: 80 g of K10-montmorillonite was added to a 1 lt. aqueous solution of $CuCl_2$ (1.0 M) under stirring. Stirring was maintained for 16–30 hrs in order to saturate the exchange capacity of K10 montmorillonite. The clay suspension was centrifuged and the supernatant solution was discarded. Washing cycles were repeated until disappearance of Cl ions from the discarded water. The clay was dried overnight in an oven at 120° C. and finely ground in a mortar.

b) Natural montmorillonite: The clay (natural montmorillonite, obtained from M S Neelakanth chemical works, Jodhpur, India) was dried at 120° C. for 24 hrs and was used.

EXAMPLE 2

A solution of benzyl alcohol (5 mmol, 0.54 g) and acetic acid (50 mmol, 3 g) was treated at reflux temperature of 116° C. in a two necked round bottom flask (50 ml) in presence of $Cu^{2-}$-montmorillonite clay (0.1 g) catalyst. After completion of the reaction (followed by TLC), 10 ml of ethyl acetate was added to the reaction mixture and the catalyst was filtered The filtrate was treated with saturated $NaHCO_3$ solution (3×10 $cm^3$) followed by water wash (2×10 $cm^3$). The resulting solution was dried upon anhydrous sodium sulfate and pure product (0.73 g) was obtained after evaporation of the solvent on rotavapor.

EXAMPLE 3

A solution of benzyl alcohol (5 mmol, 0.54 g) and acetic acid (50 mmol, 3 g) was treated at reflux temperature of 116° C. in a two necked round bottom flask (50 ml) in presence of natural montmorillonite clay (0.1 g) catalyst. After completion of the reaction (followed through TLC), 10 ml of ethyl acetate was added to the reaction mixture and the catalyst was filtered. The filtrate was treated with saturated $NaHCO_3$ solution (3×$cm^3$) followed by water wash (2×10 $cm^3$). The resulting solution was dried upon anhydrous sodium sulfate and pure product (0.74 g) was obtained after evaporation of the solvent on rotavapor.

EXAMPLE 4

A solution of trans-2-hexen-1-ol (2 mmol, 0.2 g) in dichloroethane (5 $cm^3$) was treated with acetic acid (6 mmol, 0.36 g) at reflux temperature of 80° C. in a two necked round bottom flask (50 ml) in presence of $Cu^{2+}$-montmorillonite clay (0.1 g) catalyst. After completion of the reaction (followed by TLC), the catalyst was filtered and the filtrate was treated with saturated $NaHCO_3$ solution (2×5 $cm^3$) followed by water wash (2×10 $cm_3$). The resulting solution was dried upon anhydrous sodium sulfate and pure product (0.275 g) was obtained after evaporation of the solvent on rotavapor.

EXAMPLE 5

A solution of trans-2-hexen-1-ol (5 mmol, 0.5 g) and acetic acid (50 mmol, 3 g) was treated at reflux temperature of 116° C. in a two necked round bottom flask (50 ml) in presence of natural montmorillonite clay (0.1 g) catalyst. After completion of the reaction (followed by TLC), 10 ml of ethyl acetate was added to the reaction mixture and the catalyst was filtered. The filtrate was treated with saturated NaHCO$_3$ solution (3×10 cm$^3$) followed by water wash (2×10 cm$^3$) The resulting solution was dried upon anhydrous sodium sulfate and pure product (0.69 g) was obtained after evaporation of the solvent on rotavapor.

EXAMPLE 6

A solution of octanol (2 mmol, 0.26 g) in toluene (5 cm$^3$) was treated with acetic acid (6 mmol, 0.36 g) at reflux temperature of 110° C. in a two necked round bottom flask (50 ml) in presence of Cu$^{2+}$—montmorillonite clay ( 0.1 g) catalyst. After completion of the reaction ( followed through TLC), the catalyst was filtered and the filtrate was treated with saturated NaHCO$_3$ solution (2×5 cm$^3$) followed by water wash (2×10 cm$^3$). The resulting solution was dried upon anhydrous sodium sulfate and pure product (0.34 g) was obtained after evaporation of the solvent on rotavapor.

EXAMPLE 7

A solution of octanol (5 mmol, 0.65 g) and acetic acid (50 mmol, 3 g) was treated at reflux temperature of 116° C. in a two necked round bottom flask (50 ml) in presence of natural montmorillonite clay (0.1 g) catalyst. After completion of the reaction ( followed by TLC), 10 ml of ethyl acetate was added to the reaction mixture and the catalyst was filtered. The filtrate was treated with saturated NaHCO$_3$ solution (3×10 cm$^3$) followed by water wash (2×10 cm$^3$). The resulting solution was dried upon anhydrous sodium sulfate and pure product (0.845 g) was obtained after evaporation of the solvent on rotavapor.

EXAMPLE 8

A solution of decanol (2 mmol, 0.32 g) in toluene (5 cm$^3$) was treated with acetic acid (6 mmol, 0.36 g) at reflux temperature of 110° C. in a two necked round bottom flask (50 ml) in presence of Cu$^{2+}$-montmorillonite clay ( 0.1 g) catalyst. After completion of the reaction (followed by TLC), the catalyst was filtered and the filtrate was treated with saturated NaHCO$_3$ solution (2×5 cm$^3$) followed by water wash (2×10 cm$^3$). The resulting solution was dried upon anhydrous sodium sulfate and pure product ( 0.4 g) was obtained after evaporation of the solvent on rotavapor.

EXAMPLE 9

A solution of decanol (5 mmol, 0.79 g) and acetic acid (50 mmol, 3 g) was treated at reflux temperature of 116° C. in a two necked round bottom flask (50 ml) in presence of natural montmorillonite clay (0.1 g catalyst. After completion of the reaction (followed by TLC), 10 ml of ethyl acetate was added to the reaction mixture and the catalyst was filtered. The filtrate was treated with saturated NaHCO$_3$ solution (3×10 cm$^3$) followed by water wash (2×10 cm$^3$). The resulting solution was dried upon anhydrous sodium sulfate and pure product (0.98 g) was obtained after evaporation of the solvent on rotavapor.

EXAMPLE 10

A solution of 2-octanol (5 mmol, 0.65 g) and acetic acid (50 mmol, 3 g) was treated at reflux temperature of 116° C. in a two necked round bottom flask (50 ml) in presence of natural montmorillonite clay (0.1 g) catalyst. After completion of the reaction (followed by TLC), 10 ml of ethyl acetate was added to the reaction mixture and the catalyst was filtered. The filtrate was treated with saturated NaHCO$_3$ solution (3×10 cm$^3$)followed by water wash (2×10 cm$^3$). The resulting solution was dried upon anhydrous sodium sulfate and pure product (0.84 g) was obtained after evaporation of the solvent on rotavapor.

EXAMPLE 11

A solution of amyl alcohol (5 mmol, 0.44 g) and acetic acid (50 mmol, 3 g) was treated at reflux temperature of 116° C. in a two necked round bottom flask (50 ml) in presence of natural montmorillonite clay (0.1 g), catalyst. After completion of the reaction (followed by gas chromatography), 10 ml of ethyl acetate was added to the reaction mixture and the catalyst was filtered. The filtrate was treated with saturated NaHCO$_3$ solution(3×10 cm$^3$) followed by water wash (2×10 cm$^3$). The resulting solution was dried upon anhydrous sodium sulfate and pure product (0.647 g) was obtained after evaporation of the solvent on rotavapor.

EXAMPLE 12

A solution of isoamyl alcohol (5 mmol, 0.44 g) and acetic acid (50 mmol, 3 g) was treated at reflux temperature of 116° C. in a two necked round bottom flask (50 ml) in presence of natural montmorillonite clay (0.1 g) catalyst. After completion of the reaction (followed by gas chromatography), 10 ml of ethyl acetate was added to the reaction mixture and the catalyst was filtered. The filtrate was treated with saturated NaHCO$_3$ solution (3×10 cm$^3$) followed by water wash (2×10 cm$^3$). The resulting solution was dried upon anhydrous sodium sulfate and pure product (0.64 g) was obtained after evaporation of the solvent on rotavapor.

EXAMPLE 13

A solution of 2-pentanol (5 mmol, 0.44 g) and acetic acid (50 mmol, 3 g) was treated at reflex temperature of 116° C. in a two necked round bottom flask (50 ml) in presence of natural montmorillonite clay (0.1 g) catalyst. After completion of the reaction (followed by gas chromatography), 10 ml of ethyl acetate was added to the reaction mixture and the catalyst was filtered. The filtrate was treated with saturated NaHCO$_3$ solution (3×10 cm$^3$) followed by water wash (2×10 cm$^3$). The resulting solution was dried upon anhydrous sodium sulfate and pure product (0.5 g) was obtained after evaporation of the solvent on rotavapor.

EXAMPLE 14

A solution of cinnamyl alcohol (5 mmol, 0.67 g) and acetic acid (50 mmol, 3 g) was treated at reflux temperature of 116° C. in a two necked round bottom flask (50 ml) in presence of natural montmorillonite clay (0.1 g) catalyst. After completion of the reaction (followed by TLC ), 10 ml of ethyl acetate was added to the reaction mixture and the catalyst was filtered. The filtrate was treated with saturated NaHCO$_3$ solution (3×10 cm$^3$) followed by water wash (2×10 cm$^3$). The resulting solution was dried over anhydrous sodium sulfate and pure product (0.87 g) was obtained after evaporation of the solvent on rotavapor.

EXAMPLE 15

A solution of cyclohexanol (5 mmol, 0.50 g) and acetic acid (50 mmol, 3 g) was treated at reflux temperature of 116° C. in a two necked round bottom flask (50 ml) in presence of natural montmorillonite clay (0.1 g) catalyst. After completion of the reaction (followed by TLC), 10 ml of ethyl acetate was added to the reaction mixture and the catalyst was filtered. The filtrate was treated with saturated NaHCO solution (3×10 cm³) followed by water wash (2×10 cm³). The resulting solution was dried over anhydrous sodium sulfate and pure product (0.69 g) was obtained after evaporation of the solvent on rotavapor.

EXAMPLE 16

A solution of cyclopentanol (5 mmol 0.43 g) and acetic acid (50 mmol, 3 g) was treated at reflux temperature of 116° C. in a two necked round bottom flask (50 ml) in presence of natural montmorillonite clay (0.1 g) catalyst. After completion of the reaction (followed by TLC), 10 ml of ethyl acetate was added to the reaction mixture and the catalyst was filtered. The filtrate was treated with saturated NaHCO₃ solution (3×10 cm³) followed by water wash (2×10 cm³). The resulting solution was dried over anhydrous sodium sulfate and pure product (0.63 g) was obtained after evaporation of the solvent on rotavapor.

EXAMPLE 17

A solution of 1-phenyl ethanol[α-methylbenzyl alcohol] (2 mmol, 0.24 g) in chloro benzene (5 cm³) was treated with acetic acid (6 mmol, 0.36 g) at reflux temperature of 130° C. in a two necked round bottom flask (50 ml) in presence of natural montmorillonite clay (0.1 g) catalyst. After completion of the reaction (followed by TLC), the catalyst was filtered and the filtrate was treated with saturated NaHCO₃ solution (2×5 cm³) followed by water wash (2×10 cm³). The resulting solution was dried over anhydrous sodium sulfate and pure product (0.310 g) was obtained after evaporation of the solvent on rotavapor.

EXAMPLE 18

A solution of p-methoxy-1-phenyl ethanol (2 mmol 0.304 g) in chloro benzene (5 cm³) was treated with acetic acid (6 mmol, 0.36 g) at reflux temperature of 130° C. in a two necked round bottom flask (50 ml) in presence of natural montmorillonite clay (0.1 g) catalyst After completion of the reaction (followed by TLC), the catalyst was filtered and the filtrate was treated with saturated NaHCO₃ solution (2×5 cm³) followed by water wash (2×10 cm³). The resulting solution was dried over anhydrous sodium sulfate and pure product (0.350 g) was obtained after evaporation of the solvent on rotavapor.

EXAMPLE 19

A solution of p-methyl-1-phenyl ethanol (2 mmol, 0.272 g) in toluene (5 cm³) was treated with acetic acid (6 mmol, 0.36 g) at reflux temperature of 110° C. in a two necked round bottom flask (50 ml) in presence of natural montmorillonite clay (0.1 g) catalyst. After completion of the reaction ( followed by TLC), the catalyst was filtered and the filtrate was treated with saturated NaHCO₃ solution (2×5 cm³) followed by water wash (2×10 cm³). The resulting solution was dried over anhydrous sodium sulfate and pure product (0.34 g) was obtained after evaporation of the solvent on rotavapor.

EXAMPLE 20

A solution of p-methyl-1-phenyl ethanol (5 mmol, 0.68 g) and acetic acid (50 mmol, 3 g) was treated at reflux temperature of 116° C. in a two necked round bottom flask (50 ml) in presence of natural montmorillonite clay (0.1 g) catalyst. After completion of the reaction (followed by TLC), 10 ml of ethyl acetate was added to the reaction mixture and the catalyst was filtered. The filtrate was treated with saturated NaHCO₃ solution(3×10 cm³) followed by water wash (2×10 cm³). The resulting solution was dried over anhydrous sodium sulfate and pure product ((0.87 g) was obtained after evaporation of the solvent on rotavapor.

EXAMPLE 21

A solution of furfuryl alcohol (5 mmol, 0.49 g) and acetic acid (50 mmol. 3 g) was treated at reflux temperature of 116° C. in a two necked round bottom flask (50 ml) in presence of natural montmorillonite clay (0.1 g) catalyst. After completion of the reaction (followed by TLC), 10 ml of ethyl acetate was added to the reaction mixture and the catalyst was filtered. The filtrate was treated with saturated NaHCO₃ solution (3×10 cm³) followed by water wash (2×10 cm³). The resulting solution was dried over anhydrous sodium sulfate and the solvent evaporated on rotavapor to get the crude product (0.686 g) was purified through column chromatography to get the pure product (0.4 g)

TABLE 1

Esterification of alcohols using acetic acid as acetylating agent

| Example | Alcohol (Substrate) | Ratio[a] | Catalyst | Solvent | Temp (° C.) | Time (hrs) | Product(s) | Yields[b] (%) |
|---|---|---|---|---|---|---|---|---|
| 2 | Benzyl alcohol | 1:10 | 1a | No solvent | 116 | 0.5 | Benzyl acetate | 97[c] |
| 3 | Benzyl alcohol | 1:10 | 1b | No solvent | 116 | 0.5 | Benzyl acetate | 98[c] |
| 4 | trans-2-hexene-1-ol | 1:3 | 1a | Dichloroethane | 80 | 0.15 | trans-2-hexenyl acetate | 97[c] |
| 5 | trans-2-hexene-1-ol | 1:10 | 1b | No solvent | 116 | 0.15 | trans-2-hexenyl acetate | 98[c] |
| 6 | Octanol | 1:3 | 1a | Toluene | 110 | 2.5 | Octyl acetate | 98[c] |
| 7 | Octanol | 1:10 | 1b | No solvent | 116 | 1.0 | Octyl acetate | 98[c] |
| 8 | Decanol | 1:3 | 1a | Toluene | 110 | 2.5 | Decyl acetate | 98[c] |
| 9 | Decanol | 1:10 | 1b | No solvent | 116 | 1.0 | Decyl acetate | 98[c] |
| 10 | 2-Octanol | 1:10 | 1b | No solvent | 116 | 1.5 | 2-Octyl acetate | 96[c] |
| 11 | Amyl alcohol | 1:10 | 1b | No solvent | 116 | 2.5 | Amyl acetate | 99[c,d] |
| 12 | Isoamyl alcohol | 1:10 | 1b | No solvent | 116 | 2.5 | Isoamyl acetate | 99[c,d] |
| 13 | 2-Pentanol | 1:10 | 1b | No solvent | 116 | 2.5 | 2-Pentyl acetate | 77[c,d] |
| 14 | Cinnamyl alcohol | 1:10 | 1b | No solvent | 116 | 0.2 | Cinnamyl acetate | 98[c] |
| 15 | Cyclohexanol | 1:10 | 1b | No solvent | 116 | 0.5 | Cyclohexyl acetate | 97[c] |
| 16 | Cyclopentanol | 1:10 | 1b | No solvent | 116 | 1.0 | Cyclopentyl acetate | 98[c] |
| 17 | 1-Phenyl ethanol | 1:3 | 1b | Chlorobenzene | 130 | 0.15 | 1-Phenyl ethyl acetate | 98[c] |
| 18 | p-Methoxy-1-phenyl ethanol | 1:3 | 1b | Chlorobenzene | 130 | 0.15 | p-Meo-1-phenyl ethyl acetate | 90[c] |
| 19 | p-Methyl-1-phenyl ethanol | 1:3 | 1b | Toluene | 110 | 0.15 | p-Methyl-1-phenyl ethyl acetate | 95[c] |

TABLE 1-continued

Esterification of alcohols using acetic acid as acetylating agent

| Example | Alcohol (Substrate) | Ratio[a] | Catalyst | Solvent | Temp (° C.) | Time (hrs) | Product(s) | Yields[b] (%) |
|---|---|---|---|---|---|---|---|---|
| 20 | p-Methyl-1-phenyl ethanol | 1:10 | 1b | No solvent | 116 | 0.15 | p-Methyl-1-phenyl ethyl acetate | 98[c] |
| 21 | Furfuryl alcohol | 1:10 | 1b | No solvent | 116 | 0.25 | Furfuryl acetate | 65[c] |

1a: catalyst, which is described in write-up as Example 1a
1b: catalyst, which is described in write-up as Example 1b
[a]: alcohol: acetic acid molar ratio.
[b]: based on $^1$H NMR.
[c]: isolated yields.
[d]: based on G.C analysis.

It was found that natural montmorillonite is an efficient catalyst for the exclusive formation of esters from various alcohols in the presence of acetic acid and its activity is comparable with $Cu^{2+}$-exchanged K10 montmorillonite (examples 2 to 9)

The main advantages of the present invention are:
1. The present process completely eliminates the use of expensive acetic anhydride as acetylating agent.
2. Acetic acid is used as the acetylating agent in place of the acetic anhydride for the acetylation of various substrates (aliphatic, aromatic, α,β-unsaturated, cyclic and heterocyclic alcohols) for the first time.
3. Clays have been used as catalysts in place of hazardous and corrosive $H_2SO_4$ and expensive resins for the acetylation of various alcohols for the first time.
4. An ecofriendly process for the production of esters was developed.
5. The selectivity and yields obtained in this process are excellent.
6. The reactions are simple with shorter reaction time and simple workup procedure.
7. The support of the catalyst is cheap and abundantly available in nature.
8. The present process envisage no disposal problem as the catalyst can be used for several cycles. The catalyst was subjected to four cycles which displayed consistent activity.
9. The present process is environmentally safe since there is no effluent disposable problem.

What is claimed is:
1. A process for producing esters from alcohols, which comprises:
    (A) reacting a secondary or primary $C_1$ to $C_{10}$ alcohol in a hydrous environment with acetic acid in the presence of a reusable natural montmorillonite/metal ion-exchanged clay catalyst in a solvent medium of aliphatic, aromatic, or chlorinated hydrocarbons at 30–140° C. at atmospheric pressure for a period in the range of 0.2 to 3.0 hrs, and
    (B) recovering the esters obtained from (A).
2. A process as claimed in claim 1 wherein the metal ions exchanged are selected from the group consisting of $Fe^{3+}$, $Cu^{2+}$, $Zn^{2+}$, $Al^{3+}$, $Ce^{3+}$, $Zr^{4+}$, and combinations thereof.
3. A process as claimed in claim 1 wherein the amount of acetic acid used as an acetylating agent is in the range of 3 to 11 mmls/mole of substrate.
4. A process as claimed in claim 1 wherein the alcohol used is selected from the group consisting of aromatic alcohols, aliphatic alcohols, α,β-unsaturated cyclic and heterocyclic alcohols, octanol, decanol, 2-octanol, amylalcohol, isoamylalcohol, 2-pentanol, cinnamyl alcohol, benzyl alcohol, trans-2-hexene-1-ol, cyclohexanol, cyclopentanol, 1-phenyl ethanol, p-methoxy-1-phenyl ethanol, p-methyl-1-phenyl ethanol and furfuryl alcohol.
5. A process as claimed in claim 1 wherein the solvents are selected from the group consisting of dichloroethane, toluene and chlorobenzene.
6. A process as claimed in claim 1, wherein the recovery of esters comprises:
    (A) separating the catalyst through filtration;
    (B) neutralizing the excess acetic acid by treatment with $NaHCO_3$ solution; and
    (C) removing the solvent by concentration in rotavapor.
7. A process as claimed in claim 1 wherein the recovery of esters comprises:
    (A) separating the catalyst through filtration;
    (B) neutralizing the excess acetic acid by treatment with $NaHCO_3$ solution; and
    (C) drying the resulting solution of (B).

* * * * *

UNITED STATES PATENT AND TRADEMARK OFFICE
CERTIFICATE OF CORRECTION

PATENT NO. : 6,472,555 B2
DATED : October 29, 2002
INVENTOR(S) : Choudary et al.

It is certified that error appears in the above-identified patent and that said Letters Patent is hereby corrected as shown below:

Title page,
Item [57], ABSTRACT,
Line 7, "1:3 to 11" should read -- 1:3 to 1:11 --

Column 1,
Line 33, "triofluoroacetic" should read -- trifluoroacetic --
Line 34, "cabodiimide" should read -- carbodiimide --
Line 57, "AcOH," should read -- AcOH --
Line 59, "acid treated" should read -- acid-treated --
Line 62, "an" should read -- a --
Line 64, "verticle" should read -- vertical --

Column 2,
Line 1, "to" should be deleted
Line 2, "give" should read -- gives --
Line 15, "p-nitrobezoic" should read -- p-nitrobenzoic --
Line 16, "trifluromethane" should read -- trifluoromethane --
Line 17, "resulting" should read -- resulting in --
Line 29, "were" should read -- was --
Line 30, "zirconia" should read -- zirconium --
Line 35, "an" should be deleted
Line 53, "α,⊕-unsaturated" should read -- α,β-unsaturated --

Column 3,
Line 3, "α,⊕-unsaturated" should read -- α,β-unsaturated --
Line 5, "1:3 to 11" should read -- 1:3 to 1:11 --
Line 9, "for" (first occurrence) should be deleted
Line 29, "rotavapor" should read -- Rotavapor® --
Line 58, "loose" should read -- lose --
Line 66, "Acetic" should read -- acetic --

Column 4,
Line 12, "Cl" should read -- Cl$^-$ --
Lines 32 and 45, "on" should read -- in --; and "rotavapor" should read -- Rotavapor® --
Line 55, "cm$_3$" should read -- cm$^3$ --
Line 57, "on" should read -- in --
Line 58, "rotavapor" should read -- Rotavapor® --

UNITED STATES PATENT AND TRADEMARK OFFICE
CERTIFICATE OF CORRECTION

PATENT NO. : 6,472,555 B2
DATED : October 29, 2002
INVENTOR(S) : Choudary et al.

It is certified that error appears in the above-identified patent and that said Letters Patent is hereby corrected as shown below:

Column 5,
Lines 5, 17, 30, 43 and 56, "on" should read -- in --; and "rotavapor" should read -- Rotavapor® --
Line 49, "(0.1 g catalyst." should read -- (0.1 g) catalyst. --

Column 6,
Lines 3, 17, 31, 45 and 58, "on" should read -- in --; and "rotavapor" should read -- Rotavapor® --

Column 7,
Lines 5, 18 and 32, "on" should read -- in --; and "rotavapor" should read -- Rotavapor® --

Column 8,
Lines 2, 15, 29 and 41, "on" should read -- in --; and "rotavapor" should read -- Rotavapor® --
Line 42, "was" should read -- which was --
Table 1, Example (9): "Dccanol" should read -- Decanol --
Table 1, Example (15): "Cvclohexyl" should read -- Cyclohexy --
Table 1, Example (18): "-Meo-" should read -- -Methyl- --

Column 9,
Line 44, "disposable" should read -- disposal --

UNITED STATES PATENT AND TRADEMARK OFFICE
CERTIFICATE OF CORRECTION

PATENT NO.    : 6,472,555 B2
DATED         : October 29, 2002
INVENTOR(S)   : Choudary et al.

It is certified that error appears in the above-identified patent and that said Letters Patent is hereby corrected as shown below:

<u>Column 10,</u>
Line 25, "mmls/mole" should read -- mmols/mole --
Line 43, "rotavapor" should read -- Rotavapor® --

Signed and Sealed this

Fifth Day of August, 2003

JAMES E. ROGAN
*Director of the United States Patent and Trademark Office*